(12) United States Patent
Rom (10) Patent No.: US 9,227,070 B2
(45) Date of Patent: Jan. 5, 2016

(54) CARDIAC STIMULATION WITH HEMODYNAMIC SENSOR GUARD

(76) Inventor: Rami Rom, Or-akiva (IL)

( * ) Notice: Subject to any disclaimer, the term of this patent is extended or adjusted under 35 U.S.C. 154(b) by 1526 days.

(21) Appl. No.: 12/063,245

(22) PCT Filed: Aug. 6, 2006

(86) PCT No.: PCT/IL2006/000906
§ 371 (c)(1),
(2), (4) Date: Feb. 8, 2008

(87) PCT Pub. No.: WO2007/017863
PCT Pub. Date: Feb. 15, 2007

(65) Prior Publication Data
US 2010/0198285 A1 Aug. 5, 2010

(30) Foreign Application Priority Data
Aug. 8, 2005 (GB) .................... 0516220.1

(51) Int. Cl.
| A61N 1/00 | (2006.01) |
| A61B 5/02 | (2006.01) |
| A61B 5/04 | (2006.01) |
| A61N 1/365 | (2006.01) |
| A61N 1/02 | (2006.01) |
| A61N 1/05 | (2006.01) |
| A61N 1/04 | (2006.01) |
| A61N 1/39 | (2006.01) |

(52) U.S. Cl.
CPC ............. *A61N 1/36514* (2013.01); *A61N 1/025* (2013.01); *A61N 1/046* (2013.01); *A61N 1/05* (2013.01); *A61N 1/36585* (2013.01); *A61N 1/3956* (2013.01)

(58) Field of Classification Search
CPC ........... A61N 1/36514; A61N 1/36585; A61N 1/3956; A61N 1/025; A61N 1/05; A61N 1/046
USPC ................................ 600/508–526; 607/4–38
See application file for complete search history.

(56) References Cited

U.S. PATENT DOCUMENTS

| 4,774,950 | A | * | 10/1988 | Cohen ................................ 607/6 |
| 5,417,718 | A | * | 5/1995 | Kleks et al. ...................... 607/28 |
| 5,480,412 | A | * | 1/1996 | Mouchawar et al. ............. 607/6 |
| 5,722,996 | A | * | 3/1998 | Bonnet et al. ................... 607/17 |
| 6,477,406 | B1 | * | 11/2002 | Turcott ......................... 600/518 |
| 6,477,416 | B1 | * | 11/2002 | Florio et al. ....................... 607/9 |
| 6,625,490 | B1 | * | 9/2003 | McClure et al. ................... 607/9 |
| 6,650,931 | B1 | * | 11/2003 | McClure et al. ............. 600/510 |
| 6,792,308 | B2 | * | 9/2004 | Corbucci ........................ 607/17 |
| 2005/0102002 | A1 | * | 5/2005 | Salo et al. ........................ 607/17 |
| 2007/0255151 | A1 | * | 11/2007 | Struble et al. ................. 600/513 |

* cited by examiner

*Primary Examiner* — Niketa Patel
*Assistant Examiner* — Lindsey G Hankins
(74) *Attorney, Agent, or Firm* — Mark David Torche; Patwrite LLC (57) ABSTRACT

A method and system for regulating the operation of a cardiac pacemaker or defibrillator are disclosed. A processor receives signals of both an implanted hemodynamic sensor and intra-cardiac electrograms and digitizes them. The digitized signal of the hemodynamic sensor is used to prevent inappropriate cardiac stimulation and erroneous cardiac detection. The hemodynamic signal is also used to define arrhythmias.

16 Claims, 13 Drawing Sheets

CARDIAC STIMULATION WITH HEMODYNAMIC SENSOR GUARD

CROSS-REFERENCE TO RELATED APPLICATIONS

The present application claims the benefit of priority to GB Patent Application Serial Number GB 0516220.1, filed Aug. 8, 2005, entitled "CARDIAC STIMULATION WITH HEMODYNAMIC SENSOR GUARD" and International Application Serial Number PCT/IL2006/000906, filed Aug. 6, 2006, entitled "CARDIAC STIMULATION WITH HEMODYNAMIC SENSOR GUARD", published Feb. 15, 2007, under publication number WO 2007/017863, which are incorporated herein by reference.

TECHNICAL FIELD

The present invention relates generally to cardiac pacemakers, defibrillators and implanted hemodynamic sensors and more specifically to cardiac pacing timing cycles, safety and reliability operation of implanted pacemakers and defibrillators.

BACKGROUND ART

There are two copending patent application from the author of the present invention contents of which are hereby incorporated herein by reference; first Copending PCT Patent Application Serial Number PCT/IL2004/000659, filed Jul. 20, 2004 entitled, "ADAPTIVE RESYNCHRONIZATION THERAPY SYSTEM", published Apr. 14, 2005, under publication number WO 2005/007075; second Copending PCT Patent Application Serial Number PCT/IL2006/000571, filed May 15, 2006 entitled, "VENTRICLE PACING DURING ATRIAL FIBRILLATION EPISODES".

Implanted cardiac stimulation devices, i.e. pacemakers and intracardiac cardioverter defibrillators (ICD) deliver therapy to patients suffering from various heart-diseases (Clinical Cardiac Pacing and Defibrillation, $2^{nd}$ edition, Ellenbogen, Kay, Wilkoff, 2000). Dual chamber pacemakers stimulate the right ventricle with synchrony to the sensed atrial event, with a given delay, the atrioventricular (AV) delay. Cardiac Resynchronization Therapy (CRT) devices, e.g., biventricular pacemakers, stimulate both ventricles and also synchronize the stimulation in correspondence with the sensed atrial event signal. With all implanted cardiac stimulation devices the management of the stimulation according to the accurate sensing and interpreting the electrical activity of the heart in the atria and in the ventricles is crucial for the variety of stimulation methods and algorithms. U.S. Pat. No. 6,901,291 disclose a method to distinguish between valid and invalid cardiac senses. U.S. Pat. No. 6,862,471 discloses a method for blanking T-waves from atrial cardiac signals. U.S. Pat. No. 6,912,418 discloses a system for distinguishing electrical events originating in the atria from far-field electrical events originating in the ventricles. U.S. Pat. No. 6,731,978 discloses a prioritized rule based method for detection, classification and treatment of arrhythmias.

Generally, these methods are related to the timing cycles in cardiac stimulation. The timing cycles are very important for proper operation of the implanted stimulation device and to the safety and well being of the patient. Under conditions of cardiac arrhythmias, these timing cycles become even more important and complicated to manage. In the prior art the only information used on-line are the electrical signals sensed by the implanted electrodes, i.e. the intra cardiac electrograms (IEGMs). The difficulty associated with depending solely on the IEGMs stems from the fact that the sensed signals are local and weak, having an amplitude of only several millivolts with strong coupling from ventricle to atria and ventricle to ventricle. Hence the IEGMs can be misinterpreted by the device controller which can lead to inappropriate pacing.

Implanted cardiac hemodynamic sensors are known in the art and are further developed by several manufactures, mainly for minimal invasive electrophysiological studies. In the last years few cardiac pacemaker devices included such hemodynamic sensors for hemodynamic monitoring and for creating a pacemaker system with a rate response according to hemodynamic sensors.

U.S. Pat. No. 6,865,419 proposes to use an implanted pressure sensor in order to measure the mean pulmonary arterial pressure. U.S. Pat. No. 6,882,882 proposes to use an implanted pressure sensor in order to adjust the atrioventricular delay online.

Prior art US Patent 2003/0158492 A1 presents a method for detection and treatment of myocardial ischemia based on monitoring of both the electrical and the mechanical activity of the heart in order to detect and verify more reliably the myocardial ischemia occurrence. When myocardial ischemia is detected and verified the patent suggests selecting between few options of therapy.

Prior art U.S. Pat. No. 5,458,622 A presents a method for detection, classification and treatment of pathological tachyarrhythmia from physiologic tachyarrhythmia based on implanted activity sensor.

Prior art European Patent 0488512 A2 presents an implantable hemodynamically responsive cardioverting/defibrillating pacemaker. The implantable device uses the information of the implanted hemodynamic sensor during tachycardia to select and control therapeutic means delivered such as anti-tachycardia pacing (ATP), cardioversion or defibrillation options.

Prior art US Patent 2002/0103442 A1 presents a system and a method for determining mean pulmonary arterial pressure (MPAP) using a pressure sensor located within a ventricle of a heart. The MPAP approximates the mean pressure of the pulmonary artery that can be used to optimize CRT device timings for example.

Prior art European Patent 0541338 A1 presents an implantable monitor/stimulator that monitors and assesses indices of cardiac function and automatically executes physician-selected mode of therapy with ability to increase the strength of contractility of the heart.

The prior art patents cited above use a hemodynamic sensor as a mean to detect specific heart condition (US Patent 2003/0158492), detect and treat cardiac arrhythmias (EU0488512 A2 and U.S. Pat. No. 5,458,622 A) or improve hemodynamic function (US2002/0103442 and EU0541338). The prior art patents cited above do not suggest to use the implanted hemodynamic sensor in order to prevent inappropriate cardiac stimulation or to detect erroneous cardiac events interpretation.

In the present invention a general approach and specific examples are presented that combines information from hemodynamic sensor with the information from the intracardiac electrograms for making a more reliable and safer cardiac stimulation operation. Our approach takes advantage of the fact that implanted hemodynamic sensors are being developed and implemented in implanted cardiac pacemakers and defibrillators in order to improve hemodynamic performance and to be used for future closed loop implanted devices and since such sensors become available, the present invention suggest to further use the complementary data from the hemodynamic sensor as explained in details below.

BRIEF DESCRIPTION OF THE DRAWINGS

The present invention will be understood and appreciated more fully from the following detailed description taken in conjunction with the appended drawings in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

DISCLOSURE OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1A:
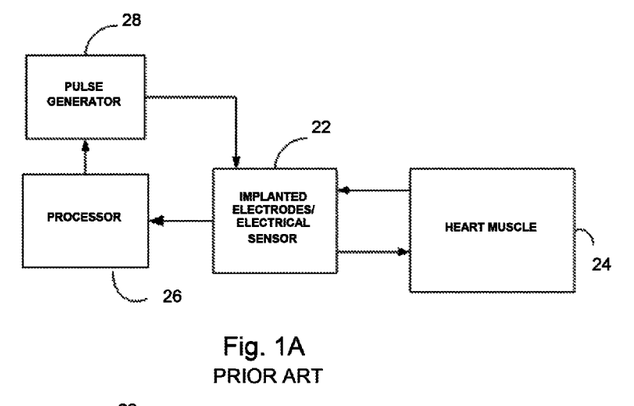
FIG. 1A is a schematic description of the interaction between the pacing device and the cardiac electrical sensors in the prior art.
Figure 1B:
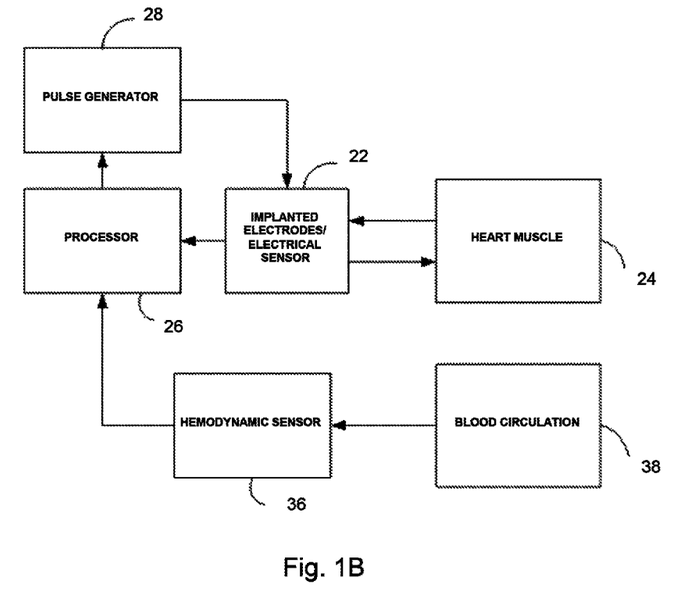
FIG. 1B is a schematic description of the interaction of the pacing device and sensors in the present invention.
Figure 1C:
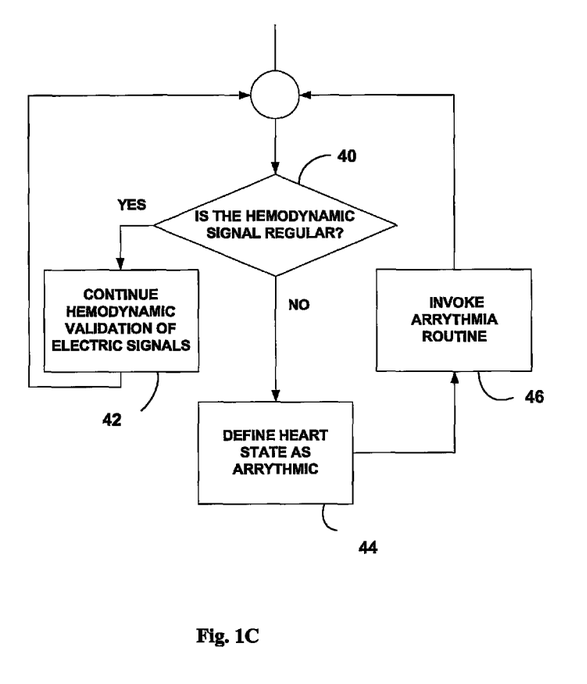
FIG. 1C is a flow diagram describing the manner of introducing hemodynamic signal regularity into the process of the invention.

In accordance with some embodiments of the present invention hemodynamic sensor signals are used to validate the electrical stimulation produced by a pacemaker or a defibrillator. To explain the application of the invention in very general terms, reference is first made to FIGS. 1A-C. In some prior art systems described in FIG. 1A electrical sensor 22 senses electrical currents in the heart muscle 24. Processor 26 reads electrical sensor 22 and accommodates to the heart's condition by generating conditioned pacing and delivering it to heart muscle 24 using a pulse generator 28. In an embodiment of the present invention described schematically in FIG. 1B, processor 26 generates pacing to heart muscle 24 but accepts conditioning signals arising from a combination of sources. Thus, electrical sensor 22 senses the electrical currents in the heart muscle 24, whereas hemodynamic sensor 36 senses parameters of the blood circulation 38. Processor 26 integrates the output signals of both types of sensors and generating conditioned pulsing stimuli through pulse generator 28 as to produce a safer and more physiologically sensible pacing. The procedure for conditioning the pacing device in accordance with the present invention is explained infra, by describing examples of specific conditions. The heart muscle pacing electrodes are also used as electrical sensors providing information as to the dynamic voltage difference between the two electrodes. Hemodynamic sensors are used for the detection or monitoring of the condition of the blood stream. For example, blood pressure, blood flow, blood oxygenation level, blood impedance as a measure of the ventricle volume. Hemodynamic sensors obtain the dynamic information required. This however does not preclude the heart itself as a site of monitoring for hemodynamic sensors, but unlike electrical sensors per se, the hemodynamic sensors in the heart collect information regarding the blood itself rather than information relating to the heart muscle. In accordance with the present invention, information about the mechanical activity of the heart obtained from an implanted hemodynamic sensor, such as a ventricle pressure sensor, is used to validate the electrophysiological information obtained from implanted electrodes that sense only the electrical activity in the heart chambers heartbeat after heartbeat. The present invention can be implemented for preventing false stimulation, validating the sensed signals and classifying arrhythmias using the time correlation between the electrical and mechanical heart activities. In FIG. 1C a flow diagram is shown depicts the manner in which the applicability and significance of the hemodynamic signal is examined. The regularity of the hemodynamic signal is examined in step 40. If the hemodynamic signal is regular, the system in step 42 continues to rely on it as a validating signal. If the signal is irregular, the heart condition is defined as arrhythmic in step 44 and an arrhythmia classification routine is invoked in step 46. Pacing therapy may or may not consequently be delivered according to the heart condition. In general terms, if the hemodynamic signal is regular it supplies complementary information relating to the heart condition to be used to detect physiologically improper pacing signals.

Figure 2A:
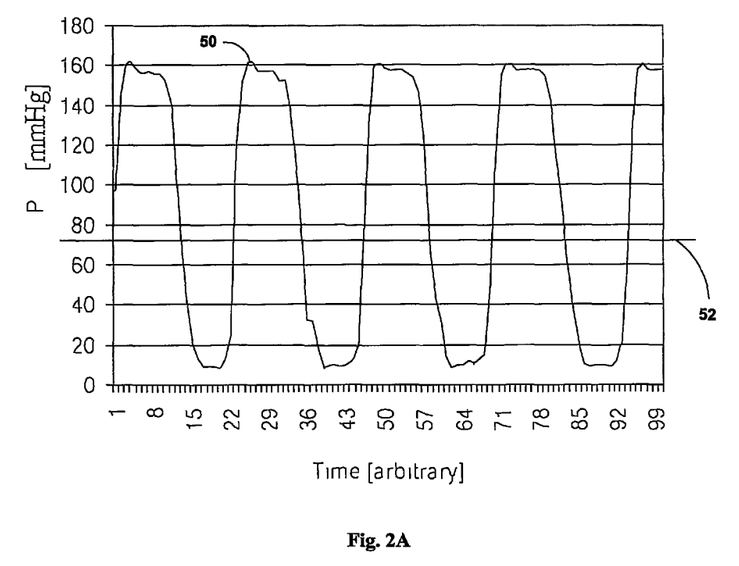
FIG. 2A is a graph showing several heartbeats in a typical ventricle pressure sensor signal.

In FIG. 2A a typical schematic ventricular pressure signal is shown having a systolic and diastolic heart cycles. The pressure wave signal, 50 is very high in magnitude during the systolic cycle, with typical maximal value reaching above 100 mmHg, highly repeatable with only small deviations from one heartbeat to the next. The pressure wave rising edge is due to the mechanical contraction of the ventricle triggered by the electrical depolarization wave (known as the R wave) and it sustains its high level during the systolic cycle. The pressure wave falling edge is due to the onset of the next diastolic cycle and it is accompanied by the electrical re-polarization wave (known as the T wave). The pressure level falls near 0 mmHg at the end of the diastolic cycle. Hence the pressure wave obtained by hemodynamic pressure sensor is highly correlated to the physiological electrical activity and at the same time clearly distinguishes between a systolic and diastolic cycles during each heartbeat. If a threshold value is defined at the half of the maximal value of the systolic pressure wave 52, a digital wave can be produced that has a logic "1" level during systolic cycle and logic "0" level during diastolic cycle. This type of digital wave generated in the pacemaker or defibrillator device controller is used in the present invention for prevention of false heart stimulation and erroneous interpretation of signals, as well as for classifying arrhythmias as is described in more detail below.

Figure 2B:
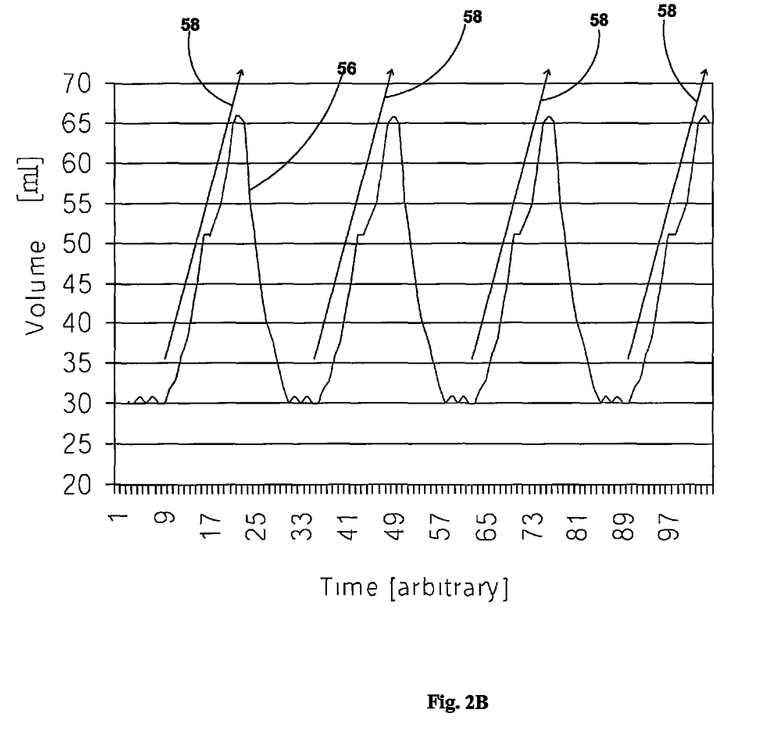
FIG. 2B is a graph showing typical impedance (ventricular volume) sensor signal giving indication regarding the measure of the cyclic change in the ventricular volume.

FIG. 2B is a typical impedance signal that reflects the ventricle volumes for several heartbeats. The impedance wave signal, 56, monotonically rises during the diastolic cycle due to the ventricle passive and active blood stream into the ventricle. Arrows, 58, designate the diastolic cycle time period. During the systolic cycle the ventricle contracts and the blood is ejected with a decrease in ventricle volume. Hence the impedance sensor signal, as the ventricle pressure signal, can be used for obtaining the systolic cycle timing and diastolic cycle timing and with this data to perform detection validation and classification of arrhythmia combined with the IEGMs as will be explained below.

Figure 3:
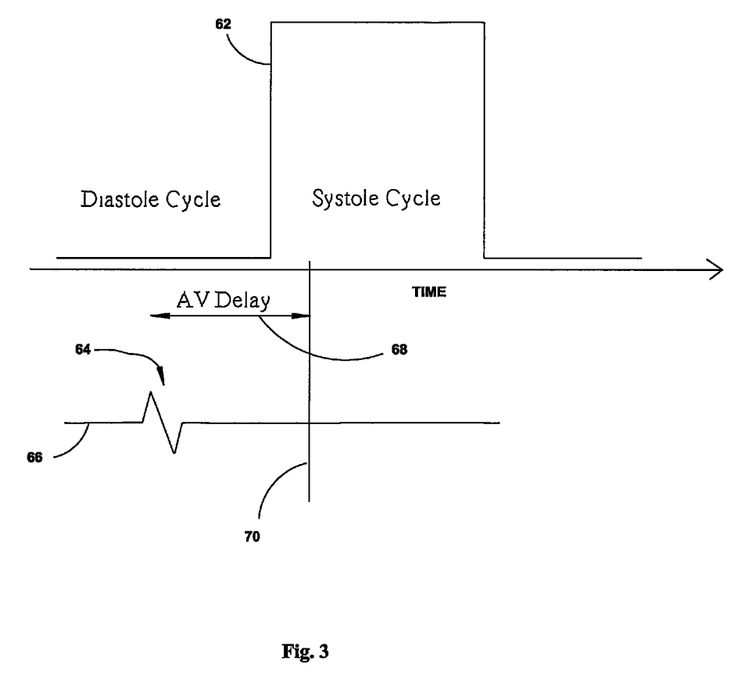
FIG. 3 is a timing diagram that shows how the pressure signal is used to prevent a false stimulation during a systole cycle.

In FIG. 3 is a timing diagram is shown illustrating the manner in which the digitized ventricle pressure signal 62 is used to prevent a false stimulation during a systolic cycle; thus preventing a dangerous ventricle arrhythmia. Ventricular pacing is delivered subsequently to a programmed AV delay measured from the last atrial event, 64, as shown in the atrial electrogram 66, in both dual chamber pacemakers and biventricular pacemakers. According to the present invention if a systolic cycle has already started and hence the digital pressure wave is at logic high level, the stimulation of the ventricle at the end of AV delay 68, as scheduled at time 70, is aborted during this heart cycle, as shown by the quiescent electrogram 66 at time 70.

Very similarly to the description above, if an impedance sensor is used as a hemodynamic sensor, stimulation during a systole may be duly aborted thus avoiding a dangerous ventricle arrhythmia. As explained above, regarding the use of a pressure sensor signal, the impedance signal can be used to obtain the digital diastolic and systolic cycles and be used prevent inappropriate pacing during the systolic cycle.

The prevention of untimely ventricular stimulation is extremely significant at such points in time in which the ventricle has just concluded its refractory period. In this type of situation, the heart is receptive and thus inappropriate stimulation may cause a dangerous ventricular tachyarrhythmia. In the prior art, prevention of untimely stimulations are brought about referencing only sensed local electrical activity, that might be a false sensing event, a far field event etc.

Figure 4:
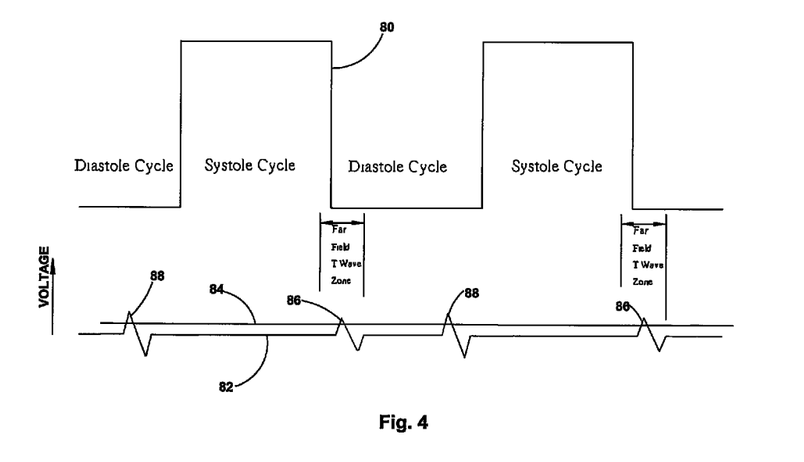
FIG. 4 is a timing diagram that shows how the digital pressure signal is used to detect a far field R wave that appear in the atrial lead signal during a diastole cycle.

In FIG. 4 a timing diagram is shown depicting the manner in which the digital pressure signal 80 is used to detect a far field T wave (known as ventricle re-polarization wave) on the atrial lead that may be mistakenly interpreted as a new P wave. The re-polarization, T wave in the ventricle lead occurs immediately after the falling edge of the ventricle pressure wave, hence it is expected to appear a few milliseconds after the initial ventricular pressure falling edge and a typical time zone can be defined including the typical time delay between onset of the T wave and the preceding pressure wave fall. The ventricle T wave is also known to generate an electrical signal in the atrial electrogram designated 82 forming due to coupling occasionally crossing the detection threshold level, 84, and hence may be interpreted erroneously as an atrial event (known as a P wave) as designated 86, whereas 88 is a valid atrial event. Hence the digital wave 80 facilitates the screening and abortion of untimely, erroneously interpreted far field T waves.

Figure 5:
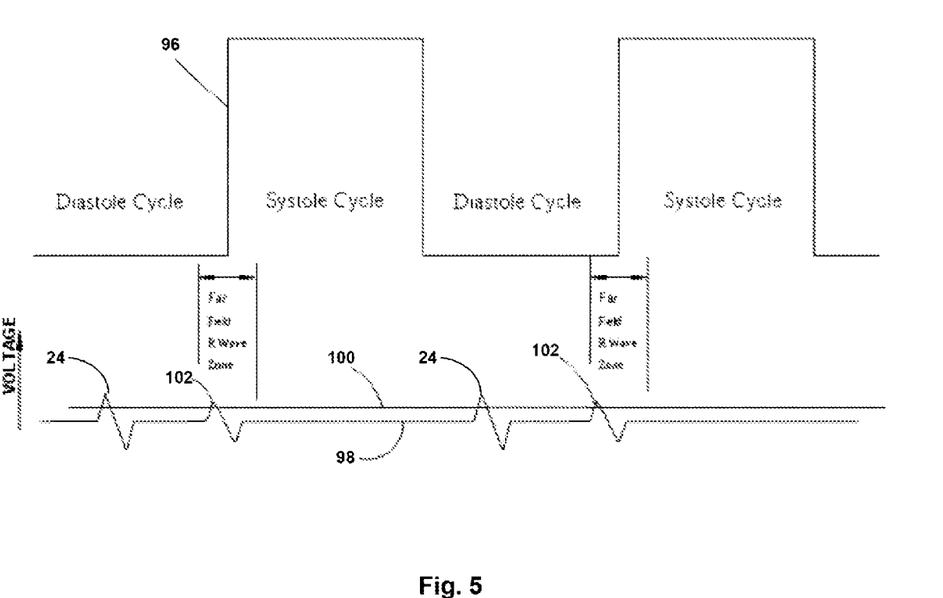
FIG. 5 is a timing diagram that shows how the digital pressure signal is used to detect a far field R wave on the atrial lead electrogram during a diastole cycle.

FIG. 5 is a timing diagram depicting the manner in which the digital pressure signal, 96, is used to detect a far field R wave on the atrial lead electrogram 98 during a diastolic cycle. The ventricle depolarization wave, known as the R wave, triggers the rising edge of the pressure wave, hence it is expected to appear a few milliseconds prior to the rising edge and a typical time zone can be defined including the typical time delay between the onset of the R wave and the pressure wave rising edge. The R wave is also known to generate an electrical signal in the atrial electrogram due to coupling that occasionally crosses the detection threshold level, 100, and could therefore be detected falsely as a new atrial event (known as a P wave) 102. In contrast, event 24 is a valid atrial event. Hence the present invention facilitates the detection and the rejection of a far field R wave occurring when the pressure wave is at low level, i.e. in diastolic cycle, just prior to its rising edge in the R wave far field time zone.

To summarize FIGS. 4 and 5, the hemodynamic sensor can be used to detect far field R and T waves. Since dual chamber pacemakers and biventricular pacemakers use the sensed atrial event as the trigger for internal counters that define the time intervals for stimulating the ventricles, such as the atrio-ventricular (AV) interval, it is of utmost importance for proper and reliable device operation to exercise the ability to differentiate between an actual atrial event that is correlated to the P wave and the far field R and T waves.

Figure 6:
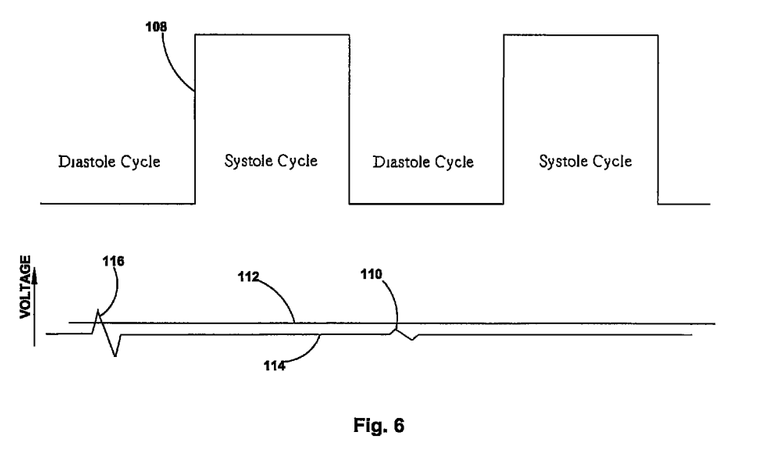
FIG. 6 is a timing diagram that shows how the digital ventricle pressure signal is used to identify a loss of atrial event sensing during a diastole cycle.

In FIG. 6 a timing diagram is shown clarifying the manner in which the pressure signal 108 is used to identify a loss of atrial event sensing during a diastolic cycle; this circumstance is known as under-sensing. When the weak atrial event signal 110 does not reach the threshold level 112 it may not be detected in the atrial electrogram 114. For the sake of clarity, a stronger atrial event 116 is shown surpassing the threshold voltage 112. If the pressure wave appears normally in the following systolic cycle, the atrial wave detection failed i.e. an under-sensing event occurred, but the overall hemodynamic performance is appropriate and there is no need for intervention. The absence of atrial event in this case can be recorded and stored for device interrogation during follow-ups. If, conversely, a pressure wave does not appear in a predefined time interval, the loss of atrial event is not an under-sensing event and device stimulation may be necessary (for instance stimulation of the atria).

Figure 7:
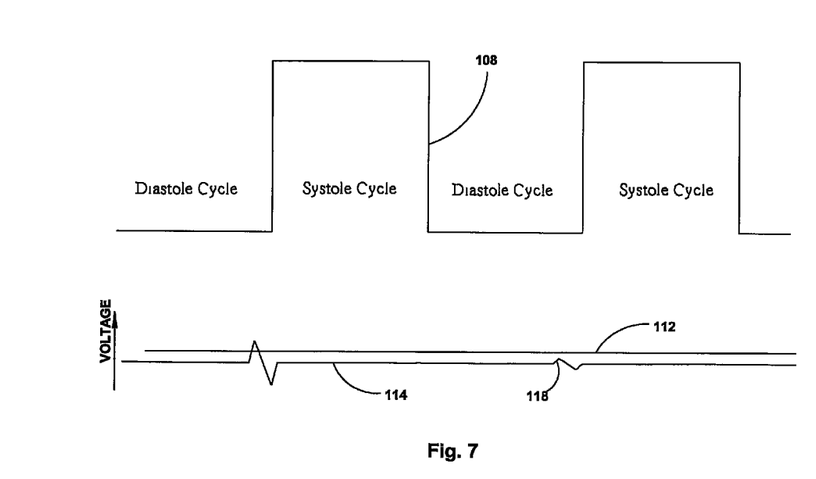
FIG. 7 is a timing diagram that shows how the digital ventricle pressure signal is used to identify a loss of ventricle event sensing during a diastole cycle.

In FIG. 7 a timing diagram depicting the manner in which the digital ventricle pressure signal 108 is used to detect loss of a ventricular event in the ventricular electrogram 114, during a diastolic cycle, when the ventricle event electrogram threshold detection level is not reached. If the pressure wave appears normally in the following systolic cycle, the ventricle event detection failed but the overall hemodynamic performance is appropriate. The absence of a ventricular event, such as an under-sensing event, can be counted and stored for device interrogation during follow-ups. If, conversely, a pressure wave does not appear normally in a predefined time interval, the loss of ventricle event is not an under-sensing event and therapy may be needed (for instance stimulation of the ventricle). Additionally, note that with the present invention if a pressure wave appeared meaning a systolic cycle is ongoing, pacing the ventricle will be prevented as described above.

Figure 8:
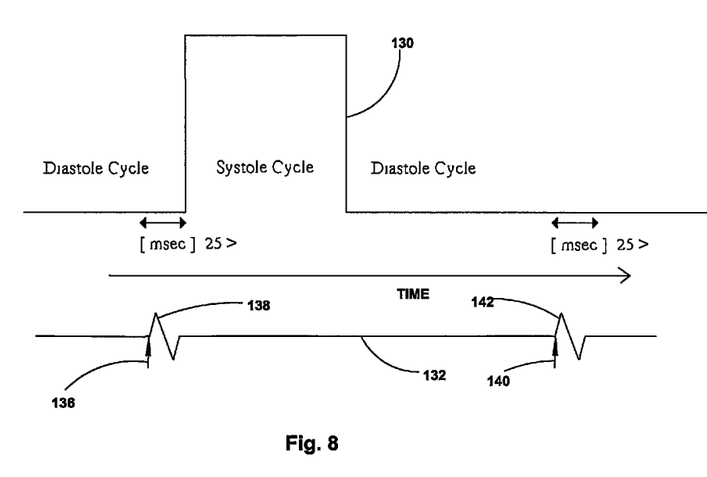
FIG. 8 is a timing diagram that shows the manner in which the loss of the digital ventricular pressure signal waveform is used to detect a capture loss of the ventricle contraction after ventricle stimulation.

In a previous Copending PCT Patent Application Serial Number PCT/IL2006/000571, filed May 15, 2006 entitled, "VENTRICLE PACING DURING ATRIAL FIBRILLATION EPISODES", from the author of the present application, content of which is hereby incorporated herein by reference, we presented a neural network architecture that performs a temporal pattern recognition applied to the hemodynamic sensor signal. The pattern recognition neural network architecture can be further used for detection of a capture loss and for detection and classification of arrhythmias as described therefrom. Reference is now made to FIG. 8, which is a timing diagram depicting the manner in which loss of digital ventricular pressure signal waveform 130 is used to detect a capture loss of the ventricle contraction subsequent to ventricle stimulation in the ventricle electrogram, 132. Following a ventricular stimulation at a specific point in time designated by arrow 136 on the time axis, an evoked response 138 is expected, the ventricle is expected to contract within a typical delay time and the ventricle contraction is expected to generate a sharp rise of the pressure wave as shown in graph 130. In contrast, after a ventricular stimulation designated by arrow 140 is followed by an evoked response 142 and loss of a sharp rise of the pressure wave as shown on graph 130, a loss of capture is detected, the evoked electrical response may be a lead depolarization due to stimulation and not an actual evoked response. The absence of a sharp pressure wave rising edge, that creates a loss of detection of the digital pressure wave, is a direct indication of a mechanical loss of capture, and hence an algorithm for detection of capture loss events can be performed using the digital pressure waveform. The advantage of the present invention method for detection capture loss events is that a direct measurement of the ventricle mechanical behaviour is taken, based on the pressure wave signal which is more reliable and repeatable compared to the weak electrical signals. Additionally, phenomena such as lead polarization due to stimulation that may be mistakenly interpreted as an evoked response are counteracted if the pressure wave is used for detection of loss of capture rather than of relying solely on electrical activity.

Figure 9:
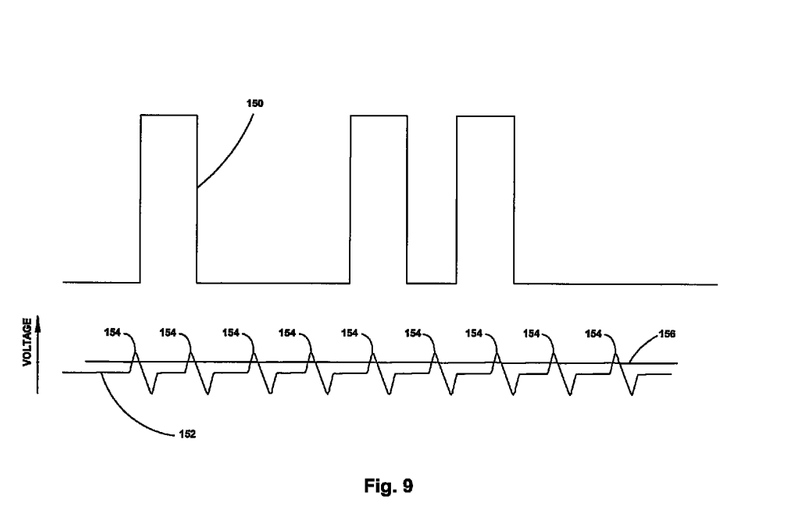
FIG. 9 is a timing diagram that shows the manner in which the ventricular pressure signal is used to identify ventricular tachyarrhythmia.

In FIG. 9 a timing diagram is shown depicting the manner in which the ventricular pressure signal, 150, is used to identify ventricular tachyarrhythmia as sensed in the ventricle electrogram 152. Ventricular events, 154 are all sensed with a high rate (low time interval between adjacent events) while the pressure wave is irregular. The reason for the irregular pressure wave is due to low maximal systolic pressure values in few heartbeats reaching below the pressure wave detection threshold. The irregular pressure wave is a very strong indication for a ventricular tachyarrhythmia that, as previously mentioned, is in sharp contrast to the pressure wave of a normal sinus rhythm which has an almost perfect periodic waveform. With detection of an irregular hemodynamic sensor signal, an arrhythmia classification routine is invoked and therapy can be delivered accordingly.

Figure 10:
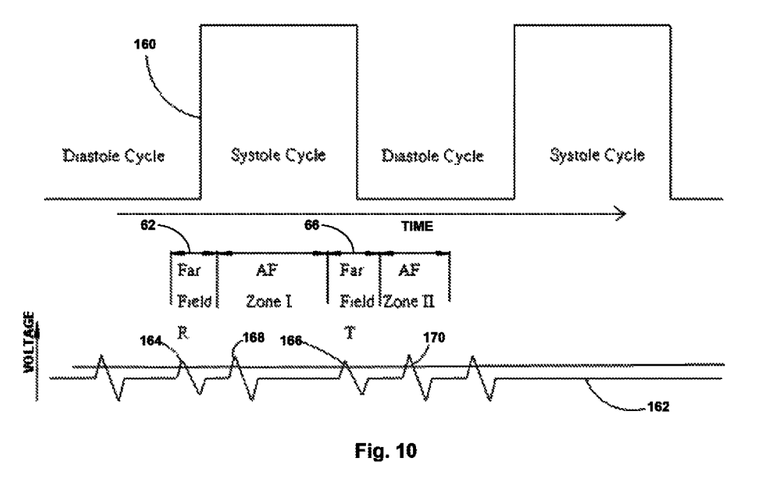
FIG. 10 is a timing diagram that shows the manner in which the digital ventricle pressure signal is used to identify atrial fibrillation.

In FIG. 10 a timing diagram is shown that depicts the manner in which the digital ventricle pressure signal 160 is used to identify atrial fibrillation as seen in the atrial electrogram 162. When the detected atrial event appears in the far field R wave zone, 62, 164 or far field T wave zone 66, 166 as shown above in FIGS. 3 and 4 to which reference is again made, the events are defined as far field events. When the detected atrial events appear in the AF zone I 168 or AF zone II 170, the events are defined as possible atrial fibrillation events, and an algorithm that counts several such consecutive AF events can determine the onset of AF.

Figure 11:
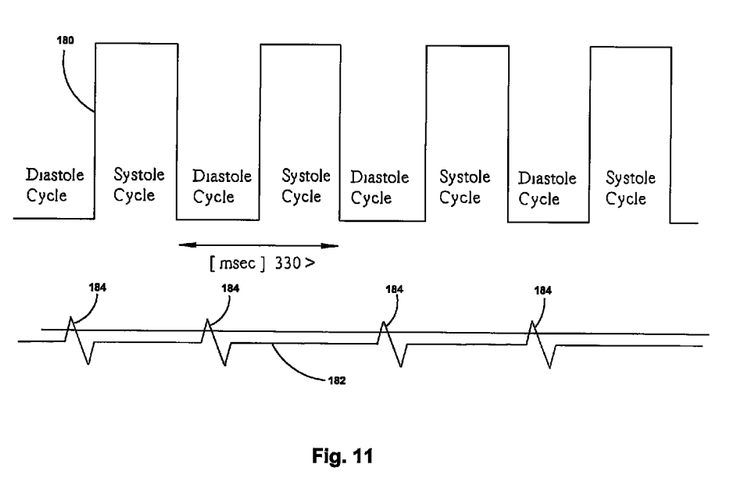
FIG. 11 is a timing diagram that shows the manner in which the digital ventricle pressure signal is used to identify atrial fibrillation.

In FIG. 11 a timing diagram is shown depicting the manner in which the ventricle digital 180 pressure signal is used to validate the onset of sinus tachyarrhythmia, seen in the atrial electrogram 182. Correlation between the systolic and diastolic cycles in the pressure wave and the atrial sensed events 184, are preserved but the heart rhythm is very high, above a predefined cut-off rate that can be programmed, for example to 180 BPM. In this example the correlation between the pressure wave and the detected atrial events used to classify a sinus tachyarrhythmia.

FIGS. 9-11 above show three examples of how the complementary information received from the hemodynamic sensor in addition to the IEGM's can be used to classify and differentiate cardiac arrhythmias. Such approach can be used also to differentiate between ventricular tachyarrhythmia (VT) and Supra ventricular tachyarrhythmia (SVT) and to deliver appropriate therapy accordingly since VT will affect significantly the signal coming from the hemodynamic sensor and will not affect the atrial electrogram while SVT that is triggered in the atria will affect both atrial IEGM and the hemodynamic sensor as was shown in FIG. 11 above.

It will be appreciated that the present invention is not limited by what has been described hereinabove and that numerous modifications, all of which fall within the scope of the present invention, exist. For instance, the hemodynamic sensor guard approach presented in this patent might be used with additional aspects of cardiac pacing by people skilled with cardiac pacemakers and defibrillators design beyond the examples given here and such applications that use complementary data from hemodynamic sensors and implanted electrocardiograms as presented here are part of this invention. The pressure sensor waveform is one example of a hemodynamic sensor that measures the mechanical behaviour of the ventricles beat after beat. The present invention is not limited to the use of ventricle pressure sensor and can be applied to other implanted hemodynamic sensors, such as ventricle impedance sensors or ventricle wall accelerometers. It is also important to note that only three examples of arrhythmias' classification were discussed with respect to examples as shown in FIGS. 9-11. The present invention can be used for an elaborate classification of different arrhythmias based on the combined and complementary information from IEGMs and hemodynamic sensors.

It will be appreciated by persons skilled in the art that the present invention is not limited by what has been particularly shown and described herein above.

The invention claimed is:

1. A method of regulating the operation of an implanted cardiac stimulation device, comprising:
   receiving signals from both an implanted hemodynamic sensor and of intracardiac electrograms by a processor;
   determining systolic pressure from the implanted hemodynamic sensor;
   integrating the received signals from the hemodynamic sensor and the intracardiac electrograms by the processor;
   detecting systolic and diastolic phases of each heartbeat using said signals; and
   generating conditioned pulsing stimuli by a pulse generator configured to prevent inappropriate cardiac pacing beat after beat,
   wherein said generating conditioned pulsing stimuli comprises producing a digital systolic pressure wave, from one heartbeat to the next, with a logic "1" level during the systolic phase and a logic "0" level during the diastolic phase based on a threshold value of the systolic pressure to distinguish between the systolic phase and the diastolic phase during each heartbeat in order to prevent ventricle pacing during a logic "1" level of the digital wave, thereby preventing inappropriate cardiac pacing beat after beat.

2. A method as in claim 1, wherein said implanted cardiac stimulation device comprises a cardiac pacemaker.

3. A method as in claim 1, wherein said implanted cardiac stimulation device comprises a cardiac defibrillator.

4. A method as in claim 1, wherein preventing inappropriate cardiac pacing beat after beat comprises detecting erroneous cardiac interpretation.

5. A method as in claim 1, further comprising detecting a far-field T wave on an atrial electrogram, based on said integrated signals.

6. A method as in claim 5, wherein said far-field T wave signal on the atrial electrogram is screened during said detected systolic phases.

7. A method as in claim 1, further comprising detecting a far-field R wave on an atrial electrogram, based on said integrated signals.

8. A method as in claim 7, wherein said far-field R wave signal on the atrial electrogram is screened during said detected systolic phases.

9. A method as in claim 1, further comprising detecting an atrial under-sensing event during said detected diastolic phase, based on said integrated signals.

10. A method as in claim 9, wherein if detecting the atrial under-sensing event did not occur during a detected diastolic phase and a subsequent systolic phase is detected, the implanted cardiac stimulation device does not stimulate the atrium, and wherein if the atrial under-sensing event did not occur during a detected diastolic phase and a subsequent systolic phase is not detected the implanted cardiac stimulation device is configured to stimulate the atrium.

11. A method as in claim 1, further comprising detecting a ventricle under-sensing event during said detected diastolic phase, based on said integrated signals.

12. A method as in claim 11, wherein if the ventricle under-sensing event did not occur during a detected diastolic phase and a subsequent systolic phase is detected, the implanted cardiac stimulation device does not stimulate the ventricle, and wherein if the ventricle under-sensing event detection did not occur during a detected diastolic phase and a subsequent systolic phase is not detected the implanted cardiac stimulation device is configured to stimulate the ventricle.

13. A method as in claim 11, wherein a loss of capture of ventricle contraction subsequent to ventricle stimulation is detected if a ventricular electrical event is detected subsequent to ventricle stimulation and a subsequent systolic phase is not detected, and wherein detection of said systolic phase is made according to the signals of said implanted hemodynamic sensor.

14. A method as in claim 1, further comprising detecting a loss of ventricle contraction by differentiating between an evoked response and lead polarization due to stimulation, based on said integrated signals.

15. A method as in claim 1, wherein preventing inappropriate cardiac pacing comprises preventing inappropriate atrial pacing during said systolic phase of the cardiac cycle.

16. A method as in claim 1, wherein the threshold value of the systolic pressure is half of the maximal value of the systolic pressure wave.

* * * * *